United States Patent
Moon

(10) Patent No.: US 10,702,024 B2
(45) Date of Patent: Jul. 7, 2020

(54) BUCKLE FOR CONNECTING STRAP AND RESPIRATOR HARNESS INCLUDING THE SAME

(71) Applicant: 3M INNOVATIVE PROPERTIES COMPANY, St. Paul, MN (US)

(72) Inventor: Jungchul Moon, Hwaseong-si (KR)

(73) Assignee: 3M Innovative Properties Company, St. Paul, MN (US)

( * ) Notice: Subject to any disclaimer, the term of this patent is extended or adjusted under 35 U.S.C. 154(b) by 268 days.

(21) Appl. No.: 15/753,031

(22) PCT Filed: Aug. 18, 2016

(86) PCT No.: PCT/US2016/047450
§ 371 (c)(1),
(2) Date: Feb. 15, 2018

(87) PCT Pub. No.: WO2017/031262
PCT Pub. Date: Feb. 23, 2017

(65) Prior Publication Data
US 2018/0235322 A1   Aug. 23, 2018

(30) Foreign Application Priority Data
Aug. 20, 2015  (KR) .......... 10-2015-0117270

(51) Int. Cl.
*A44B 11/00*   (2006.01)
*A62B 18/02*   (2006.01)
(Continued)

(52) U.S. Cl.
CPC ........ *A44B 11/006* (2013.01); *A41D 13/1161* (2013.01); *A61M 16/0683* (2013.01);
(Continued)

(58) Field of Classification Search
CPC ....... A44B 11/006; A44B 11/06; A44B 11/20; A44B 11/24; A62B 18/02; A62B 18/025;
(Continued)

(56) References Cited

U.S. PATENT DOCUMENTS 3,839,738 A * 10/1974 Coslett .................... A42B 3/08
2/421
4,555,815 A   12/1985 Walther
(Continued)

FOREIGN PATENT DOCUMENTS

CN   201941551 U   10/2010
EP        260959      9/1987
(Continued)

OTHER PUBLICATIONS

Supplementary European Search Report for Application EP16837798 dated Mar. 15, 2019.
(Continued)

*Primary Examiner* — Joseph D Boecker

(57) ABSTRACT

The present disclosure relates to a buckle for connecting a strap and a respirator harness including the same. In particular, according to one aspect of the present disclosure, a buckle for connecting a strap including a coupler configured to extend from one position, a strap connector at which a strap connecting hole is formed, wherein the strap connecting hole is connected to a strap which is connected to a mask body, and a hooking portion connected to the one position and including a surface configured to face the coupler, wherein a tap of a helmet or a tap of a head cradle is accommodated between the coupler and the hooking portion so that a position thereof is fixed, and a respirator harness including the same are provided.

18 Claims, 12 Drawing Sheets

(51) Int. Cl.
*A62B 18/08* (2006.01)
*A41D 13/11* (2006.01)
*A61M 16/06* (2006.01)
*A42B 3/28* (2006.01)
*A61M 16/10* (2006.01)

(52) U.S. Cl.
CPC ......... *A61M 16/105* (2013.01); *A62B 18/025* (2013.01); *A62B 18/084* (2013.01); *A42B 3/288* (2013.01)

(58) Field of Classification Search
CPC .. A62B 18/04; A62B 18/084; A61M 16/0488; A61M 16/0683; A42B 3/08; A42B 3/288; A41D 13/1161; B63C 2011/128
See application file for complete search history.

(56) References Cited

U.S. PATENT DOCUMENTS

| | | | |
|---|---|---|---|
| 5,193,368 A | 3/1993 | Ling | |
| 5,970,526 A | 10/1999 | Weathers | |
| 6,389,606 B1 | 5/2002 | Galet | |
| 2004/0221432 A1 | 11/2004 | Nezu | |
| 2006/0016050 A1 | 1/2006 | Yoshiguchi | |
| 2007/0157439 A1* | 7/2007 | Schmidtke | A62B 18/084 24/298 |
| 2009/0293243 A1 | 12/2009 | Yoshiguchi | |
| 2010/0319701 A1 | 12/2010 | Connell | |
| 2011/0265796 A1* | 11/2011 | Amarasinghe | A61M 16/06 128/206.28 |
| 2014/0216476 A1* | 8/2014 | Brace | A62B 18/084 128/863 |
| 2014/0311494 A1* | 10/2014 | Gibson | A61M 16/0683 128/206.21 |
| 2015/0201725 A1 | 7/2015 | Kljajic | |
| 2017/0065036 A1* | 3/2017 | Castiglione | A41D 13/1161 |

FOREIGN PATENT DOCUMENTS

| | | | | |
|---|---|---|---|---|
| EP | 0297234 | | 9/1991 | |
| GB | 2013770 A | * | 8/1979 | ............. A44B 11/26 |
| JP | 7034706 | | 6/1995 | |
| KR | 2002-01877 | | 11/2000 | |
| KR | 2003-38228 | | 1/2004 | |
| KR | 1020130049180 | | 5/2013 | |
| WO | WO 2007-106010 | | 9/2007 | |
| WO | WO 2009/059353 | | 5/2009 | |
| WO | WO 2014/120440 | | 8/2014 | |
| WO | WO 2017-031262 | | 2/2017 | |

OTHER PUBLICATIONS

International Search Report for PCT International Application No. PCT/US2016/047450, dated Nov. 14, 2016, 3 pages.

* cited by examiner

BUCKLE FOR CONNECTING STRAP AND RESPIRATOR HARNESS INCLUDING THE SAME

CROSS REFERENCE TO RELATED APPLICATIONS

This application is a national stage filing under 35 U.S.C. 371 of PCT/US2016/047450, filed Aug. 18, 2016, which claims the benefit of Korean Application No. 10-2015-0117270, filed Aug. 20, 2015, the disclosure of which is incorporated by reference in its/their entirety herein.

BACKGROUND

Field of the Invention

The present disclosure relates to a buckle for connecting a strap and a respirator harness including the same.

Discussion of Related Art

A respirator is a device for protecting a wearer from inhaling contaminants existing in a surrounding environment, and it is used by being tightly worn on a nose and a mouth of the wearer so as to separate contaminated surrounding air from an inside of a mask in which fresh air exists. At this point, the mask may be used to filter air passing therethrough. Such a respirator is used in various industrial fields including construction, manufacture, vehicle painting and repairing, medicine manufacturing, surgery, and the like.

In such a respirator, a strap connected to both ends of the mask is coupled to a head cradle which is provided to be worn on a head of a wearer, and the mask is tightly attached to and maintained on a face of the wearer by means of the head cradle. As such, a member for maintaining a mask body on the face of the wearer while the wearer is using the respirator is commonly referred to as a harness.

One example of a harness used in a typical respirator is disclosed in Korean Laid-Open Patent Publication No. 10-2013-0049180 ("Patent Document 1").

The harness disclosed in Patent Document 1 includes a flexible strap and a head cradle connected thereto, and the head cradle includes first and second lateral direction extending members and is configured to enable the first and second lateral direction extending members to be seated on and supported by a head of a wearer while the wearer is wearing a respirator.

At this point, the flexible strap is connected to the head cradle through a buckle, and is provided to connect a mask body and the head cradle to each other on a lateral side of each of the head cradle and the mask body of the respirator. Also, the flexible strap is provided to be adjustable in its length at the buckle so that the wearer may adjust a length of the strap so as to fit it to a head size of the wearer.

SUMMARY OF THE INVENTION

However, the conventional technique described above has the following problems.

In industrial fields in which a respirator is used, most workers wear helmets for safety, and, when a worker wants to wear a respirator and a helmet together, because there is no means for connecting the respirator to the helmet, the worker should additionally wear the helmet while wearing a head cradle on his or her head. Consequently, the head of the worker is excessively pressurized due to wearing the head cradle and the helmet that overlap each other, such that the worker inevitably feels uncomfortable. Further, because the helmet does not come into close contact with the head of the worker, there is a problem in that a cushioning may not properly act when an impact is applied to the head of the worker.

Also, when a worker wants to take off only a respirator while wearing both the respirator and a helmet, there is an inconvenience in that the worker first takes off the helmet to place it at a certain position and then takes off a head cradle and the respirator, after which he/she puts the helmet back on.

To address the problems described above, an object of embodiments of the present disclosure is to provide a head cradle and a respirator harness capable of being commonly attached to and detached from a helmet and enabling a taking off of the respirator with a simplified manipulation.

According to one aspect of the present disclosure, a buckle for connecting a strap may be provided, wherein the buckle includes a coupler configured to extend from one position, a strap connector at which a strap connecting hole is formed, wherein the strap connecting hole is connected to a strap which is connected to a mask body, and a hooking portion connected to the one position and including a surface configured to face the coupler, wherein a tap of a helmet or a tap of a head cradle is accommodated between the coupler and the hooking portion so that a position thereof is fixed.

Embodiments of the present disclosure may be universally attachable to and detachable from a head cradle and a helmet without causing discomfort for a wearer, and may provide an effect in that a respirator is put on and taken off with simplified manipulation to be comfortable for the wearer while wearing the helmet.

DETAILED DESCRIPTION OF EXEMPLARY EMBODIMENTS

Hereinafter, a concrete embodiment for realizing the spirit of the present disclosure will be described in detail with reference to the drawings. It should be noted that the drawings are not illustrated to scale for convenience of a description. Also, in the following description of the present disclosure, if a detailed description of known configurations and functions is determined to obscure the interpretation of embodiments of the present disclosure, the detailed description thereof will be omitted.

Figure 1:
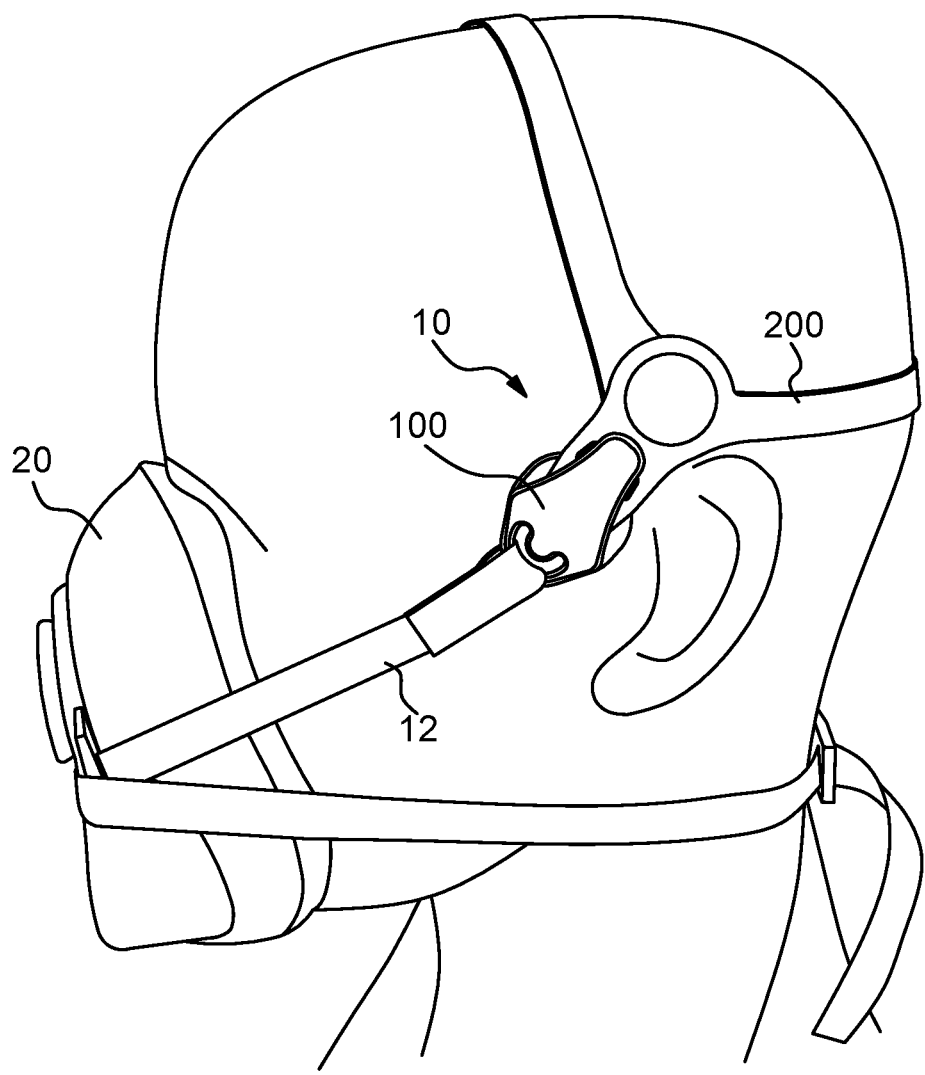
FIG. 1 is a diagram illustrating a state in which a respirator harness including a buckle according to a first embodiment of the present disclosure and coupled to a mask body is worn on a head of a wearer.

FIG. 1 is a diagram illustrating a state in which a respirator harness including a buckle according to a first embodiment of the present disclosure and coupled to a mask body is worn on a head of a wearer.

With reference to FIG. 1, a buckle 100 according to one embodiment of the present disclosure may be used in a respirator mask 1 which is a device that tightly contacts a nose and above a mouth of a wearer so as to protect the wearer from inhaling contaminants existing in a surrounding environment. The respirator mask 1 may include a mask body 20 that comes into contact with a face of the wearer when being worn to block foreign material flowing into the respirator, and a harness 10 fixing the mask body 20 to a head of the wearer.

Particularly, the harness 10 may include a strap 12 connected to both sides of the mask body 20, a head cradle 200 that comes into close contact with the head of the wearer, and the buckle 100 connecting the strap 12 to the head cradle 200.

Figure 6:
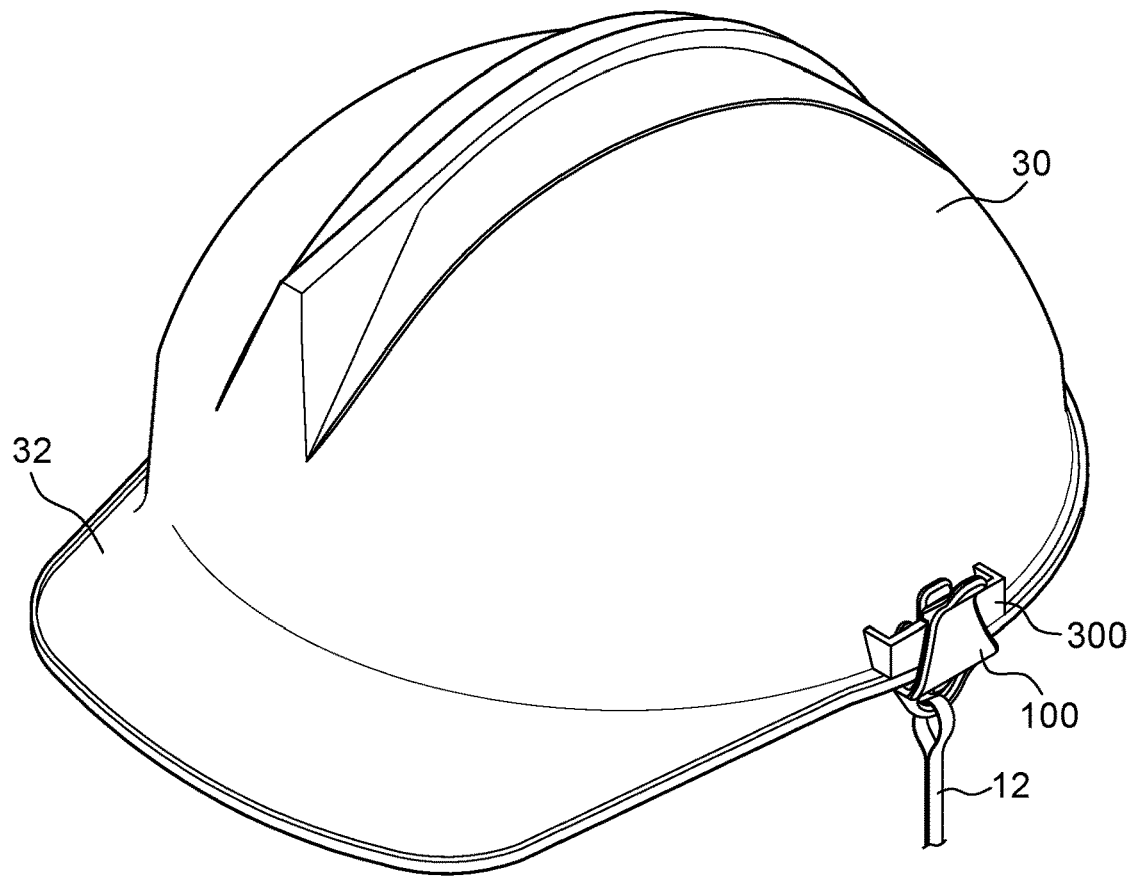
FIG. 6 is a perspective view illustrating a state in which the buckle of FIG. 1 is coupled to a helmet.

Meanwhile, the buckle 100 may be used for not only connecting to the respirator mask 1 in which the harness 10 is used, but connecting the mask body 20 to a helmet 30, which is shown in FIG. 6, and a concrete embodiment related thereto will be described later.

The mask body 20 may be formed to occlude the mouth and the nose of the wearer, and may be include a protruding part so as not to cause discomfort for the wearer.

Also, the mask body 20 may include a filter capable of filtering air that the wearer inhales. For example, the mask body 20 may include a filtering structure having one or more filtering layers, and a supporting structure for supporting the filtering structure and maintaining an appearance. At this point, the filtering structure may be made in a sheet form, and may have various other shapes and configurations.

In addition, the filtering structure may include a fluid permeable surface region through which air passes when the wearer inhales or exhales.

Additionally, the filtering structure may be a particle-capturing filter or a gas and vapor filter. In some cases, the mask body 20 may further include an exhalation valve (not shown) connected to the filtering structure to rapidly eliminate air that the wearer exhales from an inside of a mask, and the exhalation valve may be formed at a central portion of the mask body 20.

One end of the strap 12 may be connected to one lateral portion of the mask body 20, and the other end thereof may be connected to the buckle 100. Also, when an external force is applied, the strap 12 may extend over two times a total length of the strap 12 and may have elasticity so as to restore to its original state when the external force is released.

The strap 12 at each of both sides of the mask body 20 may extend to a predetermined length and may be connected to a tap 210, which is shown in FIG. 4, of the head cradle 200, or a tap 300, which is shown in FIG. 6, of the helmet 30 by means of the buckle 100 at both sides of the head of the wearer. At this point, tension may be generated at the strap 12 by a restoring force of the strap 12 having elasticity and the mask body 20 may come into close contact with the face of the wearer by means of such tension of the strap 12.

For example, the strap 12 may have a length in a range of about 25 to 60 cm, a width in a range of 5 to 10 mm, and a thickness in a range of 0.9 mm to 1.5 mm.

Also, the strap 12 may be manufactured from various materials, for example, a thermosetting rubber, a thermoplastic elastomer, a combination of a braided or knitted yarn and a rubber, an inelastic braided component, and the like.

Meanwhile, the buckle 100 may be connected to the strap 12 at one side of the buckle 100, may be selectively coupled to the tap 210 of the head cradle 200 and the tap 300 of the helmet 30 at the other side of the buckle 100, and may be configured to be easily attachable and detachable with a simplified manipulation by the wearer. Hereinafter, a detailed configuration of such a buckle 100 will be described with reference to FIGS. 2 and 3.

Figure 2:
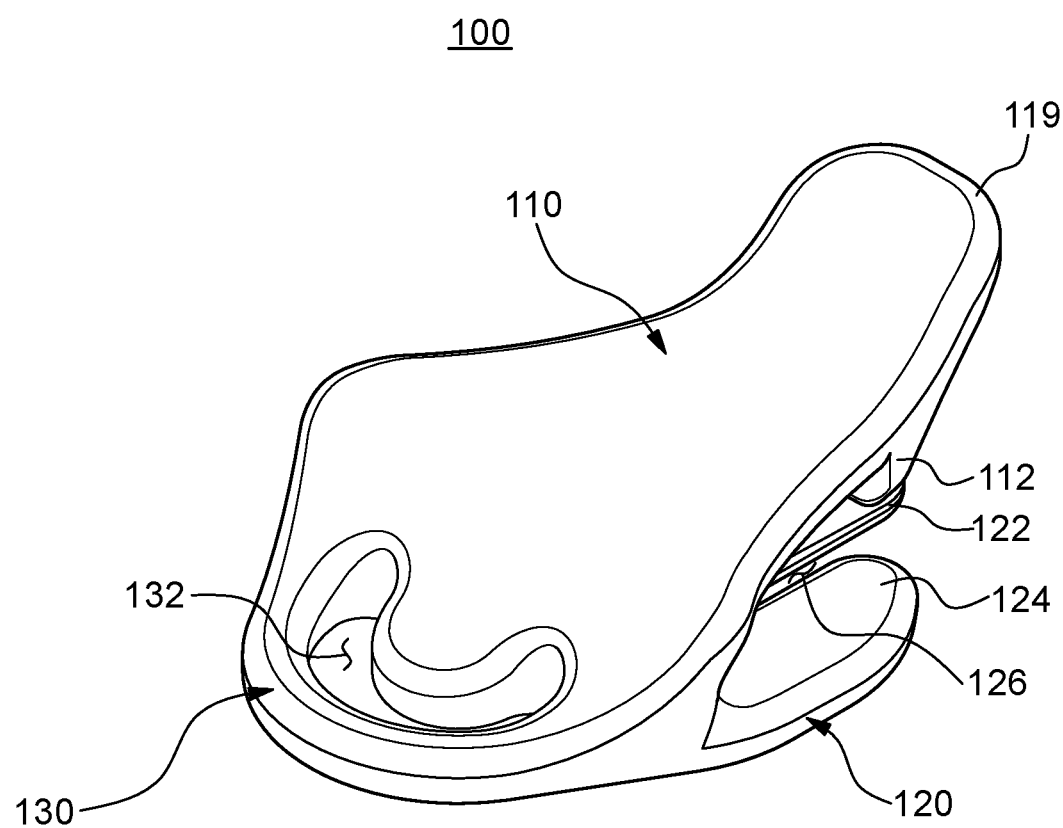
FIG. 2 is a perspective view illustrating the buckle of FIG. 1.
Figure 3:
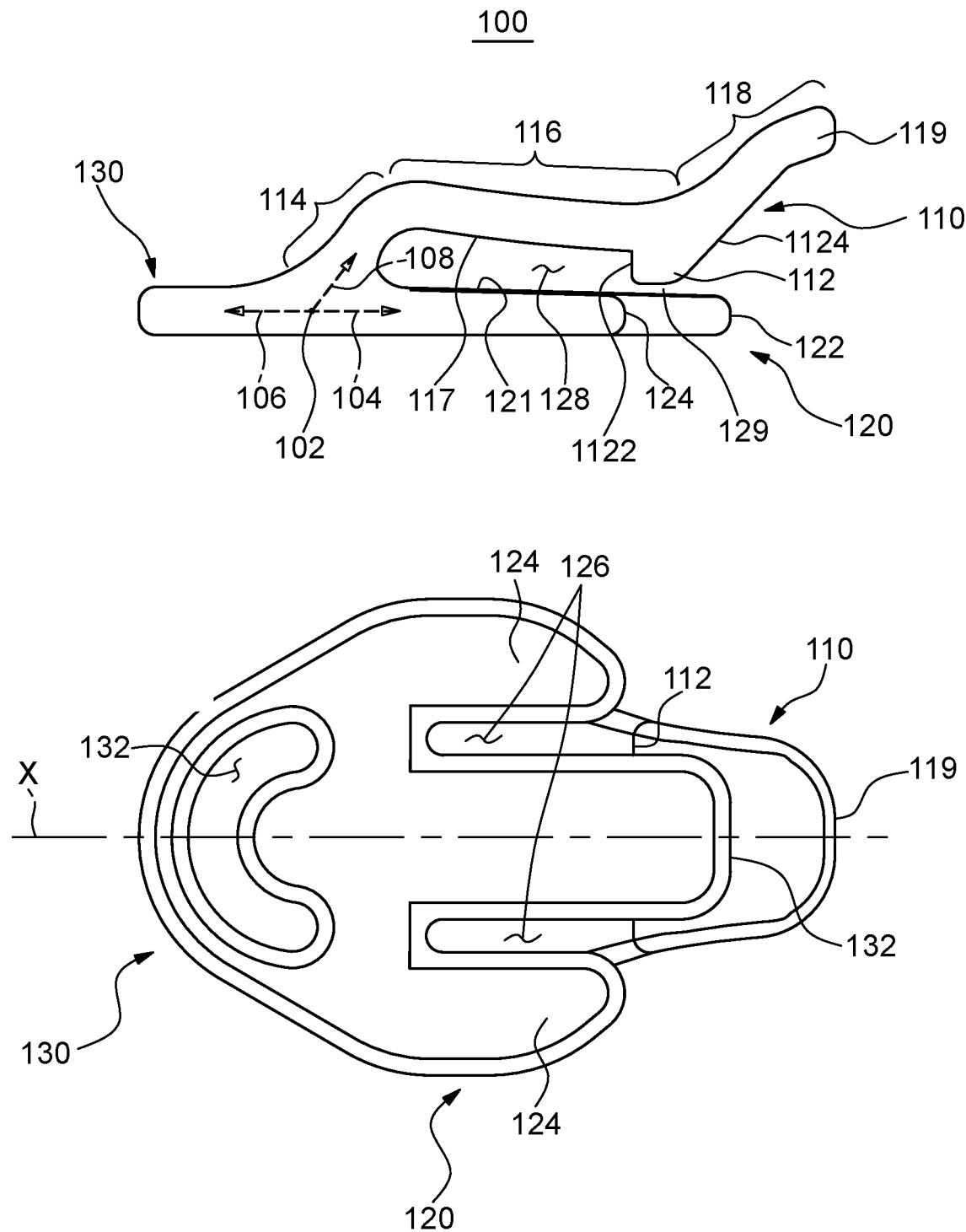
FIG. 3 is a lateral side view and a bottom view illustrating the buckle of FIG. 1.

FIG. 2 is a perspective view illustrating the buckle of FIG. 1, and FIG. 3 is a lateral side view and a bottom view illustrating the buckle of FIG. 1.

With reference to FIGS. 2 and 3, the buckle 100 may be made as a single piece, and may be provided to be coupled to the tap 300 formed at a side part of the helmet 30 to connect the strap 12, which is connected to the mask body 20, to the helmet 30, or may be provided to be coupled to the tap 210 formed at an end part of the head cradle 200 to connect the head cradle 200, which comes into close contact with the head of the wearer, to the strap 12.

Also, the buckle 100 may be made from a material having flexibility, and, for example, from a polymer-based plastic material having flexibility.

In particular, the buckle 100 may include a coupler 120 extending from one position 102 in a first direction 104, a strap connector 130 extending from the one position 102 in a second direction 106, and a hooking portion 110 formed to protrude from the one position 102 in a third direction 108 so as to include a surface facing the coupler 120. At this point, the first direction 104 and the second direction 106 are opposite directions to each other, but this is merely an example and the spirit of the present disclosure is not limited thereto.

The coupler 120 is inserted into an inner space of the tap 300 formed at a lateral portion of the helmet 30 when it is being coupled to the helmet 30, whereas the coupler 120 comes into close contact with the tap 210 of the head cradle 200 when it is being coupled to the head cradle 200.

Also, one or more coupling depressions 126 may be formed at the coupler 120 by being formed to be concave in the second direction 106 from an end of the first direction 104 and passing through with respect to both surfaces of the coupler 120. Such a coupling depression 126 may enable the coupler 120 to be inserted into the inner space of the tap 300 by corresponding to a shape of the tap 300 of the helmet 30, which will be described later, and in addition, may serve a function for guiding the insertion of the coupler 120.

In particular, the coupler 120 may be configured with a plurality of parts that are divided by the coupling depression 126, and, in the present embodiment, a case in which the coupler 120 is configured with three divided parts that are divided by two coupling depressions 126 has been shown as an example. Here, the above described example merely follows the shape of the tap 300 of the helmet 30, which is generally used, and the number of coupling depressions 126 and the number of divided parts of the coupler 120 may be varied according to a shape of the helmet 30 to which the buckle 100 is applied.

In the present embodiment, the coupler 120 may be configured to be divided into the three divided parts by the two coupling depressions 126, and these divided parts may correspond to a central coupling member 122 and side coupling members 124 formed at both sides of the central coupling member 122, respectively.

All end parts of the central coupling member 122 and the side coupling members 124 may undergo a rounding treatment which is intended to eliminate discomfort caused by an angular shape of the end part when the buckle 100 is gripped by hand to be coupled to the helmet 30 or the head cradle 200. However, the spirit of the present disclosure is not limited thereto.

In addition, such an end part shape of each of the central coupling member 122 and the side coupling members 124 may ease the coupling of the buckle 100 because an end part of the tap 300 of the helmet 30 or an end part of the tap 210 of the head cradle 200 may smoothly climb over a rounded portion of the end part of each of the coupling members 122 and 124 when a wearer couples the buckle 100 to the tap 300 of the helmet 30 or the tap 210 of the head cradle 200 even though the wearer is trying to insert the coupler 120 by approximately setting a position thereof.

Further, when being viewed on the basis of the bottom view of FIG. 3, each of the side coupling members 124 may be made of one lateral surface of a straight line shape, which configures the coupling depression 126, and the other lateral surface of a curved shape. In particular, the curved shape may be a shape in which a width of the side coupling member 124 gradually narrows toward its end part. However, such a shape of the side coupling member 124 is merely an example and the spirit of the present disclosure is not limited thereto, and a shape of the side coupling member 124 may be freely modified depending on a situation within a range that does not depart from the spirit of the present disclosure.

Also, the coupling depression 126 may be formed at a constant width along the first direction 104 except two end parts that underwent the rounding treatment, and may be symmetrically formed with respect to an imaginary central line X along the first direction 104. As a result, the shapes of the central coupling member 122 and the side coupling members 124 may be symmetrically formed with respect to the central line X.

In addition, a surface 121 facing the hooking portion 110 of the coupler 120 may be formed to be inclined, wherein a cross sectional area of the surface 121 gradually narrows in the first direction 104. Although the surface 121 of the coupler 120 may rub against the tap 300 of the helmet 30 or the tap 210 of the head cradle 200 when the buckle 100 is coupled to the helmet 30 or the head cradle 200, such a shape of the coupler 120 may minimize a contact area at this point, thereby the wearer may have a smooth feeling when he or she inserts the coupler 120.

Meanwhile, the hooking portion 110 may be formed to extend from the one position 102 of the buckle 100 in the third direction 108. At this point, the third direction 108 may be formed to lean more in the first direction 104 than the second direction 106. In other words, an angle between the third direction 108 and the first direction 104 may be smaller than that between the third direction 108 and the second direction 106. Consequently, the hooking portion 110 may extend to include a surface 117 forming a gently curved surface and also facing the coupler 120.

At this point, a connection part between the hooking portion 110 and the coupler 120 may be formed to have a gently rounded shape at an inner side and an outer side of the connection part, and, with such a shape, a nice appearance may be secured and also an area of the connection part between the hooking portion 110 and the coupler 120 may be widened, thereby configuring the connection part not to be easily disconnected.

Also, the tap 300 of the helmet 30 or the tap 210 of the head cradle 200 is inserted into a separated space 128, a portion of which is surrounded by the surface 117 facing the coupler 120 of the hooking portion 110 and the surface 121 facing the hooking portion 110 of the coupler 120, so that the buckle 100 may be coupled to the helmet 30 or the head cradle 200.

Such a hooking portion 110 includes a hook protrusion 112 formed to protrude from the surface 117 facing the coupler 120 toward the coupler 120. At this point, the hook protrusion 112 may be formed to protrude in order to narrow an opening in the first direction 104 of the separated space 128.

Also, in order to reduce a cross sectional area along a protruding direction, an inward wall 1122 of the hook protrusion 112 may be formed to have a step with respect to the surface 117 facing the coupler 120 of the hooking portion 110, and an outward wall 1124 of the hook protrusion 112 may be formed to be inclined with respect to the inward wall 1122 thereof. With such a shape of the hook protrusion 112, when the buckle 100 is coupled to the tap 300 of the helmet 30 or the tap 210 of the head cradle 200, the tap 300 of the helmet 30 or the tap 210 of the head cradle 200 climbs over the outward wall 1124 of the hook protrusion 112 to be hooked at the step of the inward wall 1122 so that a coupled state may be maintained.

An entire shape of the hooking portion 110 may be formed with a plurality of curved portions extending toward each other, and since each curved portion has a curved shape, the hooking portion 110 includes a curved surface facing the coupler 120 and an opposite curved surface. At this point, the curved surfaces included in each curved portion may have different curvatures from each other.

In particular, the hooking portion 110 may include a protruding curved portion 114 protruding from the one position 102 meeting the coupler 120, an opposing curved portion 116 extending from the protruding curved portion 114, and an extending curved portion 118 extending from the opposing curved portion 116.

The protruding curved portion 114 is formed to be curved in the third direction 108 in a direction close to the coupler 120. Also, the opposing curved portion 116 extending from the protruding curved portion 114 may include the surface 117 facing the coupler 120, and may be formed with a curvature smaller than that of the protruding curved portion 114.

Further, the extending curved portion 118 may extend to protrude toward outside farther than the coupler 120 with respect to the first direction 104, and the hook protrusion 112 may protrude from a connecting position between the opposing curved portion 116 and the extending curved portion 118. Consequently, an opening 129 may be formed in the vicinity of the end of the coupler 120 in the first direction 104 of the separated space 128 narrowed by the hook protrusion 112.

Through the opening 129 formed as described above, the tap 300 of the helmet 30 or the tap 210 of the head cradle 200 may be inserted into the separated space 128, and, when the insertion into the separated space 128 is completed, the tap 300 of the helmet 30 or the tap 210 of the head cradle 200 may be maintained in a hooked state by means of the hook protrusion 112.

At this point, the buckle 100 may be made of a material having flexibility as described above, and the hooking portion 110 included in the buckle 100 may also have flexibility. Consequently, the tap 300 of the helmet 30 or the tap 210 of the head cradle 200, which has a thickness greater than a width of the opening 129, is inserted through the opening 129, the hook protrusion 112 is moved back by the tap 300 of the helmet 30 or the tap 210 of the head cradle 200 such that the hooking portion 110 is bent in a direction in which the opening 129 is widened, and, after the insertion is completed and thus a force pushing the hook protrusion 112 is released, the hooking portion 110 is restored to its original shape and the hook protrusion 112 is hooked at the tap 300 of the helmet 30 or the tap 210 of the head cradle 200.

Meanwhile, an end part 119 of the extending curved portion 118 corresponding to an end part of the hooking portion 110 may be curved to approach the coupler 120. As described above, the end part 119 of the extending curved portion 118 is curved toward the coupler 120 so that a maximum height of the buckle 100 is lowered based on the lateral side view of FIG. 3 in comparison with a case of it being formed not to be curved. With such a configuration, when a wearer puts on the respirator mask 1 using the buckle 100, the buckle 100 may be prevented from severely protruding in left and right directions of a head of the wearer.

As such, when the buckle 100 is used in a general industrial field in which other equipment including a welding shield, ear protection, and the like in addition to the mask body 20 is required to be worn on a portion of a face, a problem of the mask body 20 interfering with a member supporting other equipment on a head of the wearer may be lessened.

Meanwhile, the strap connector 130 is formed at an opposite side of the coupler 120 of the buckle 100, and a strap connecting hole 132 through which the strap 12 passes to be connected is formed at the strap connector 130. After the strap 12 passes through the strap connecting hole 132, the passed end part of the strap 12 may be joined to another part thereof to be connected to the buckle 100 so as not to be separated.

At this point, a joining means of the strap 12 may be bonding using an adhesive as one example, but the spirit of the present disclosure may not be limited to this joining means of the strap 12.

The strap connecting hole 132 may be formed in a semicircular shape as one example, and when formed in such a semicircular shape, an available space in which the strap 12 is movable with respect to the buckle 100 may be provided. Consequently, when the wearer wears the respirator mask 1 using the buckle 100, a relative position of the strap 12 with respect to the helmet 30 or the head cradle 200 may be freely changed according to a wearing position of the helmet 30 or the head cradle 200, shapes of a head and a face of the wearer, and the like.

Each of the hooking portion 110, the coupler 120, and the strap connector 130 of the buckle 100, which have been described above, may have a symmetrical shape with respect to the imaginary central line X. As described above, the buckle 100 is configured as a single piece to have a left and right symmetrical shape so that it has an advantage of being able to be easily manufactured through an injection molding manner using a mold that is easily manufactured with left and right symmetry.

Hereinafter, a principle in which the buckle 100 configured as described above is easily coupled to the helmet 30 and the head cradle 200 will be described in order. Firstly, with reference to FIGS. 4A, 4B, and 5, a principle in which the buckle 100 is coupled to the head cradle 200 will be described.

Figure 4A:
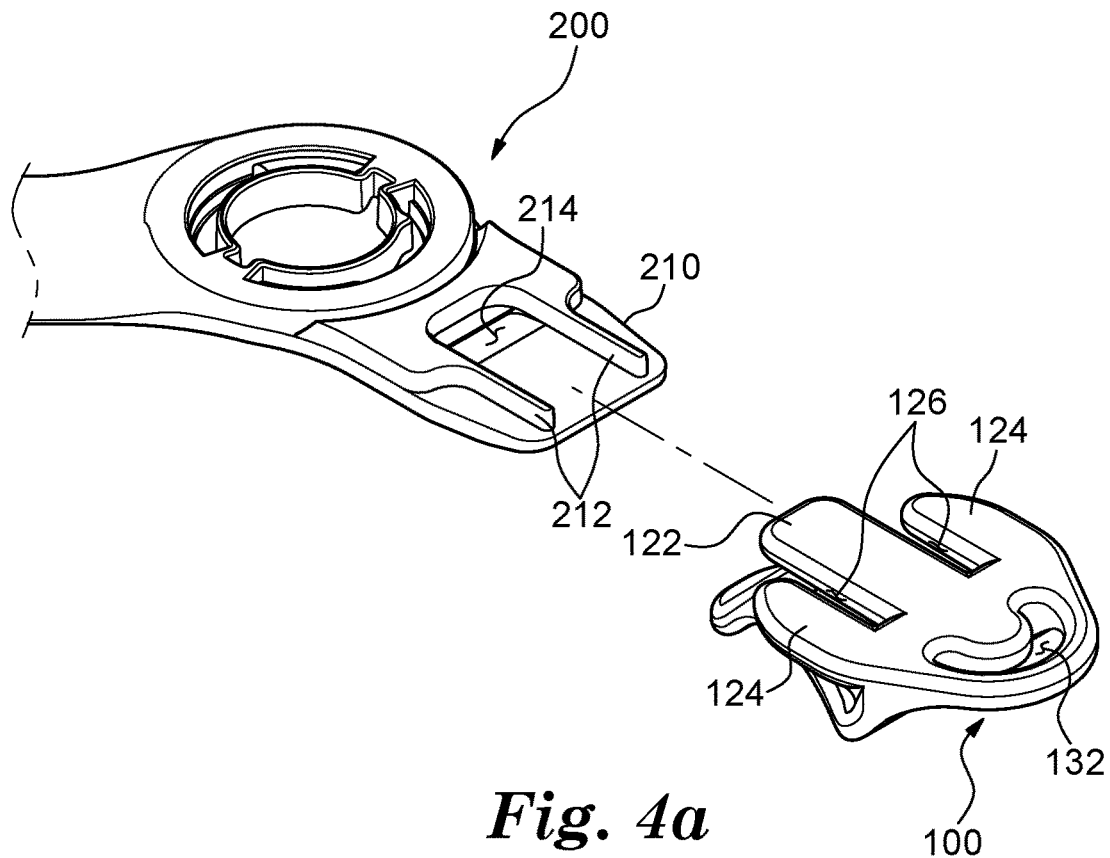
FIGS. 4A and 4B are diagrams illustrating a state in which the buckle of FIG. 1 is coupled to a head cradle.
Figure 4B:
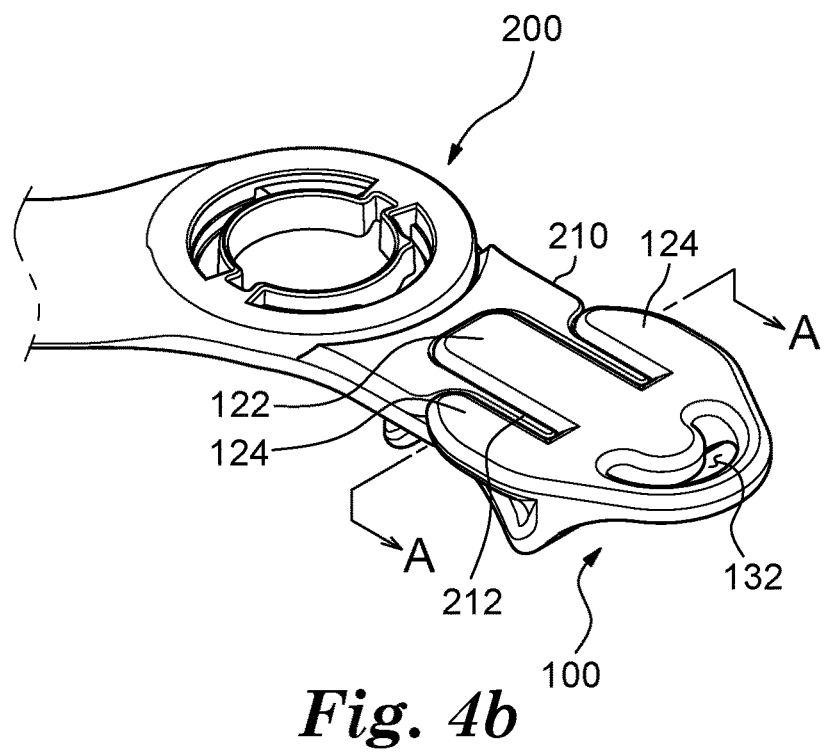
Figure 5:
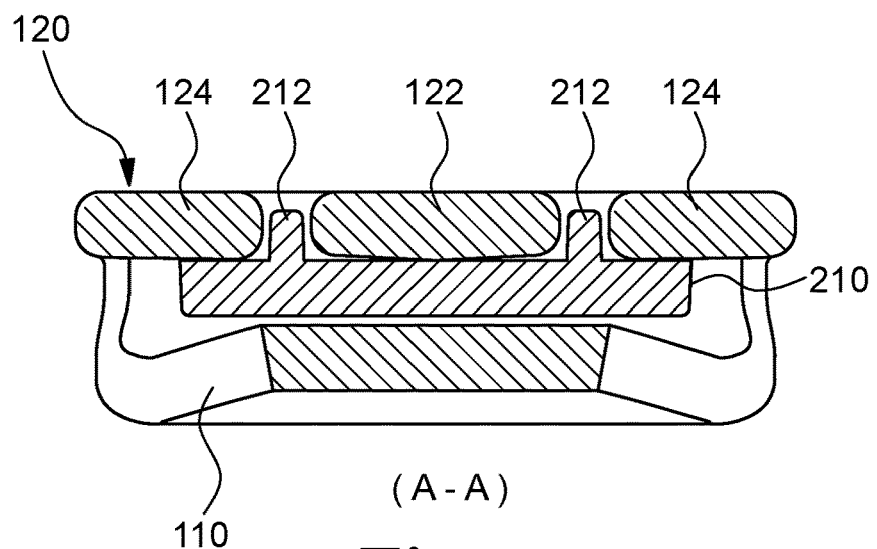
FIG. 5 is a cross-sectional view illustrating a cross section take along line A-A of the buckle and the head cradle of FIG. 4B.

FIGS. 4A and 4B are diagrams illustrating a state in which the buckle of FIG. 1 is coupled to a head cradle, and FIG. 5 is a cross-sectional view illustrating a cross section take along line A-A of the buckle and the head cradle of FIG. 4B.

With reference to FIGS. 4A, 4B, and 5, the head cradle 200 comes into close contact with a head of a wearer to serve to maintain the mask body 20, which is connected through the buckle 100 and the strap 12, to be in close contact with a face of the wearer. For this purpose, the head cradle 200 may include two supporting members which are connected at both sides so as to be respectively opened at a predetermined angle.

The tap 210 of the head cradle 200, which extends from a point at which the two supporting members are connected to each other, may have a structure coupleable to the buckle 100. In particular, the tap 210 of the head cradle 200 may include a protruding member 212 having a shape corresponding to the coupling depression 126 of the buckle 100 and protruding from one surface to be formed at a position corresponding thereto. At this point, the protruding member 212 may be formed with a thickness the same as a width of the coupling depression 126 along a direction extending along the one surface of the tap 210 of the head cradle 200.

For example, two protruding members 212 may be formed corresponding to the two coupling depressions 126 formed at the coupler 120 of the buckle 100, and the central coupling member 122 of the coupler 120 may be inserted into a space between the two protruding members 212. In other words, the protruding members 212 are inserted into the coupling depressions 126 when the buckle 100 is coupled to the coupler 120 so that a relative position of the buckle 100 with respect to the head cradle 200 may be fixed.

Also, a hooking hole 214, in which the hook protrusion 112 of the buckle 100 may be accommodated when the buckle 100 is coupled to the head cradle 200, may be formed at the tap 210 of the head cradle 200.

In addition, a surface opposite to the surface at which the protruding member 212 of the head cradle 200 protrudes may be formed to be inclined at a predetermined angle so as to gradually reduce a cross sectional area of the tap 210 of the head cradle 200 toward an outside thereof. Consequently, when the buckle 100 is coupled to the tap 210 of the head cradle 200, the hook protrusion 112 may smoothly move forward along the inclined surface, and the opening 129 of the separated space 128 is not abruptly opened when the hook protrusion 112 moves forward so that the possibility of damage to the connection part between the coupler 120 and the hooking portion 110 may be reduced.

A process of coupling the buckle 100 to the tap 210 of the head cradle 200 having the shape described above will be described as follows. The buckle 100 in a state of being gripped by a wearer may approach the tap 210 of the head cradle 200 in the first direction 104. When the hook protrusion 112 of the buckle 100 begins to move forward along the inclined surface of the tap 210 of the head cradle 200, the opening 129 may be widened due to the flexibility of the buckle 100 at the same time that the central coupling member 122 may enter a space between the protruding members 212.

As described above, if the buckle 100 is continuously moved forward toward the tap 210 of the head cradle 200 and thus the hook protrusion 112 is accommodated in the hooking hole 214, the hooking portion 110 which is bent to widen the opening 129 is again restored so that the hook protrusion 112 is hooked at a side wall configuring the hooking hole 214. In other words, as the hook protrusion 112 is accommodated in the hooking hole 214, the inward wall 1122 of the hook protrusion 112 comes into contact with the side wall of the hooking hole 214.

As a result, the process of coupling the buckle 100 to the head cradle 200 may be completed, and the protruding member 212 is accommodated in the coupling depression 126 at the same time that the hook protrusion 112 is accommodated in the hooking hole 214 so that the coupled state of the buckle 100 with respect to the head cradle 200 may be maintained.

As described above, by simply entering the buckle 100 toward the tap 210 of the head cradle 200 to allow the coupling to be completed, the wearer is able to easily couple the buckle 100 while wearing the head cradle 200 on his or her the head, thereby being able to wear the mask body 20 on his or her face.

In addition, when the coupling to the buckle 100 is released so as to take off the head cradle 200, the buckle 100 may be moved forward in a reverse direction against when the coupling was made to be easily separated by pulling the extending curved portion 118 of the hooking portion 110 to cause a state in which the opening 129 is artificially widened. Consequently, when wanting to change the head cradle 200 with the helmet 30 in a state of wearing the head cradle 200, the wearer may be able to first separate the buckle 100 to take off the head cradle 200 and then to wear the helmet 30, thereby coupling the buckle 100 to the helmet 30 again so that there may be an advantage of being easily able to perform the change.

Hereinafter, a principle of coupling the buckle 100 to the helmet 30 will be described with reference to FIGS. 6 to 8.

Figure 7:
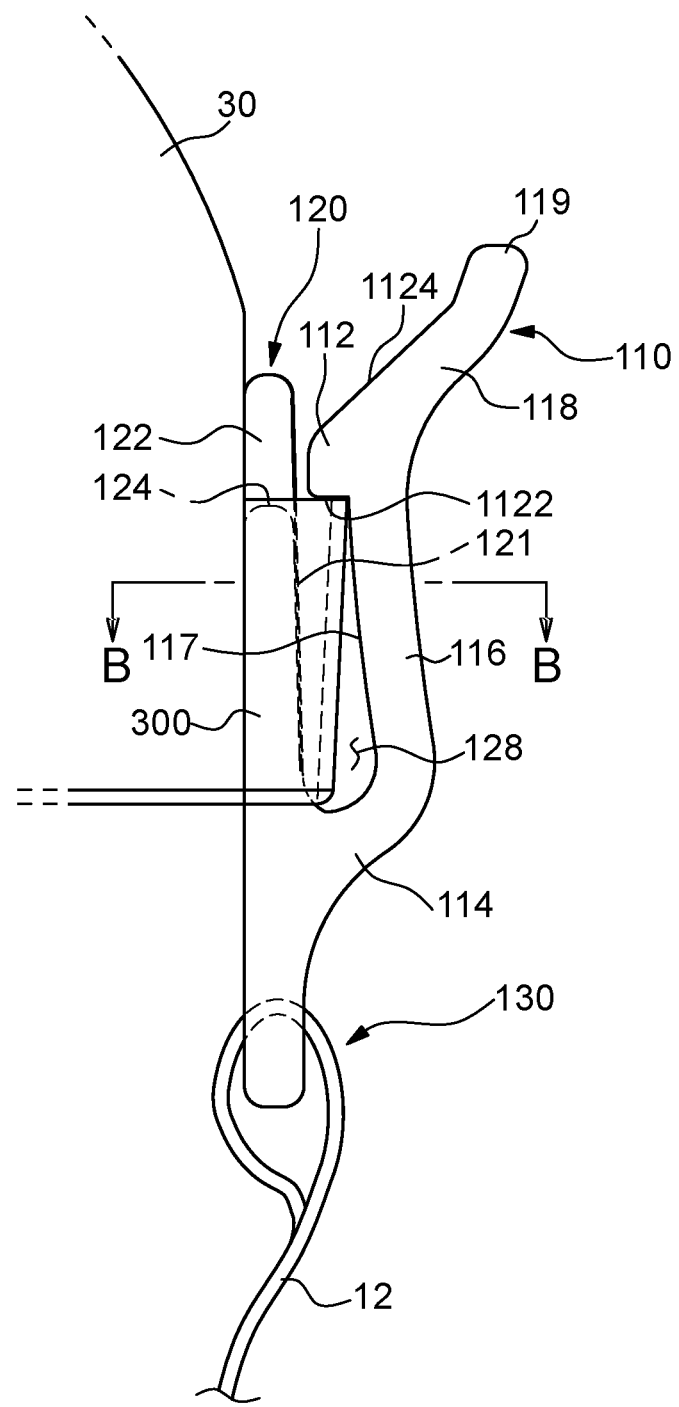
FIG. 7 is a front view illustrating a state in which the buckle of FIG. 1 is coupled to the helmet.
Figure 8:
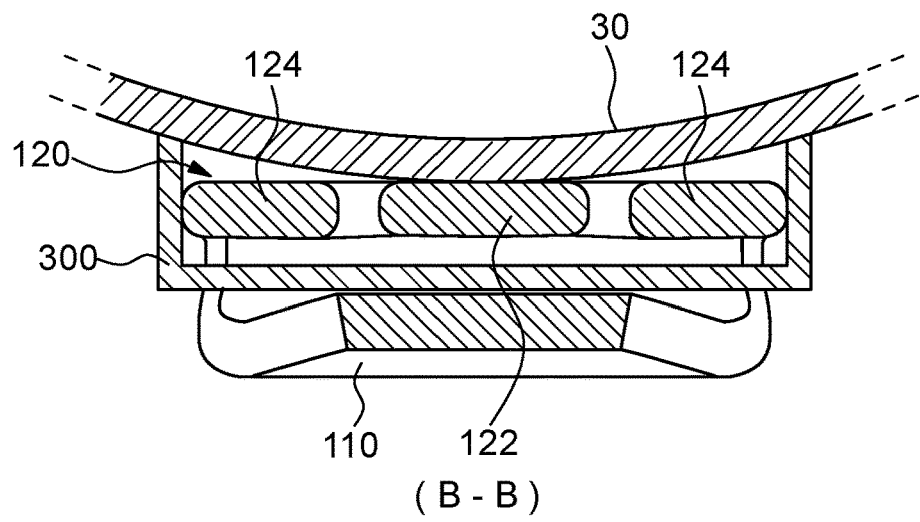
FIG. 8 is a cross-sectional diagram illustrating a cross section taken along line B-B of the buckle and the helmet of FIG. 7.

FIG. 6 is a perspective view illustrating a state in which the buckle of FIG. 1 is coupled to a helmet, FIG. 7 is a front view illustrating a state in which the buckle of FIG. 1 is coupled to the helmet, and FIG. 8 is a cross-sectional diagram illustrating a cross section taken along line B-B of the buckle and the helmet of FIG. 7.

With reference to FIGS. 6 to 8, the helmet 30 is worn on a head of a wearer to protect the head thereof from an external impact. Typically, such a helmet 30 is frequently worn and used together with equipment including a welding shield, ear protection, and the like. For fixing such equipment to the helmet 30, the tap 300 may be typically formed at both lateral parts of the helmet 30 being used in industrial fields.

The tap 300 may have a shape including therein a through hole which passes therethrough in upward and downward directions of the helmet 30, and may be formed at a lower end part of the helmet 30. Also, the through hole of the tap 300 map pass a curved lateral side surface itself of the helmet 30. In addition, the through hole of the tap 300 may be a shape having a cross section of a quadrangle.

The buckle 100 is coupled to such a tap 300, which is formed, of the helmet 30 so that the strap 12 connected to the mask body 20 is connected to the helmet 30, and thus the mask body 20 is supported by the helmet 30, thereby maintaining a state of being in close contact with a face of the wearer.

In particular, the wearer may move the buckle 100 forward toward the tap 300 from a downward side to an upward side to enter the coupler 120 of the buckle 100 into an inner space of the tap 300 when coupling the buckle 100 to the helmet 30. When the entering of the coupler 120 into the tap 300 begins, the hooking portion 110 is bent to widen the opening 129 and the hook protrusion 112 climbs over an inward wall surface of the tap 300 to be slidably entered therein.

When the hook protrusion 112 arrives at an upper surface of the tap 300, the bent hooking portion 110 is again restored and the inward wall 1122 of the tap 300 comes into contact with the upper surface thereof, and consequently, the hook protrusion 112 is hooked at the tap 300 to complete a coupling of the buckle 100.

As described above, in the present embodiment, the buckle 100 is coupleable to the helmet 30 without the head cradle 200 so that it may attain effects of convenience in use and also more safety against an external impact in comparison with a typical respirator harness structure in which the helmet 30 is worn in a state in which the head cradle 200 is worn.

Hereinafter, a second embodiment of a buckle of the present disclosure will be described with reference to FIGS. 9 to 12.

Figure 9:
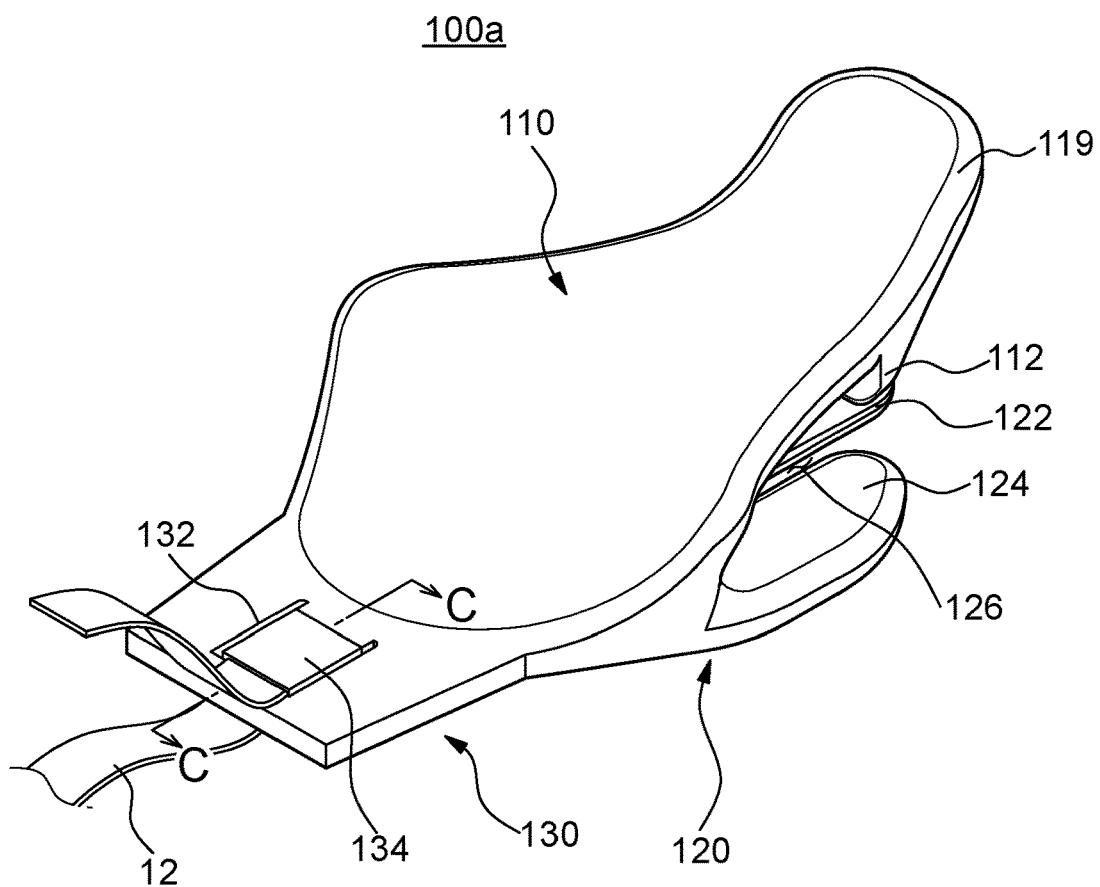
FIG. 9 is a perspective view illustrating a state in which a strap is coupled to a buckle according to a second embodiment of the present disclosure.
Figure 10:
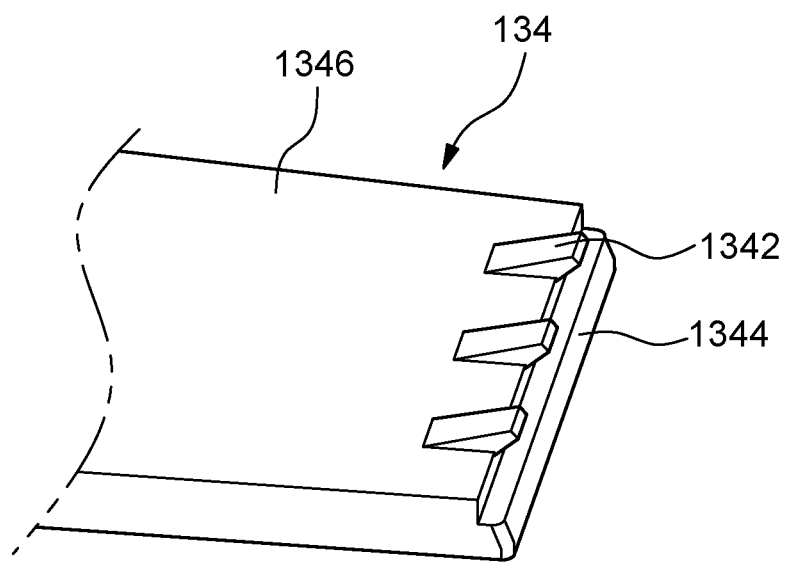
FIG. 10 is a perspective view illustrating a strap gripping protrusion formed at a fixing flap included in the buckle of FIG. 9.
Figure 11:
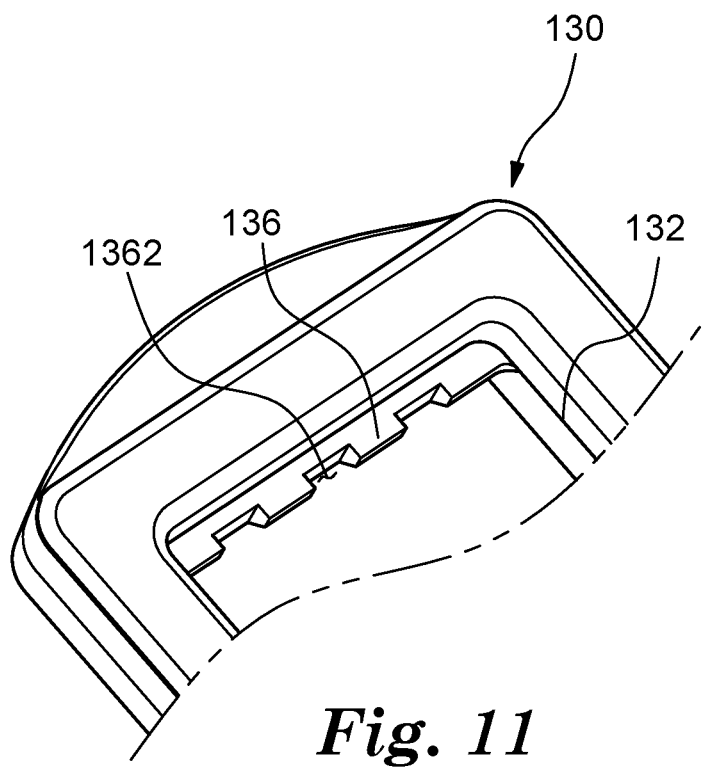
FIG. 11 is a diagram enlarging a strap connector of FIG. 9.
Figure 12:
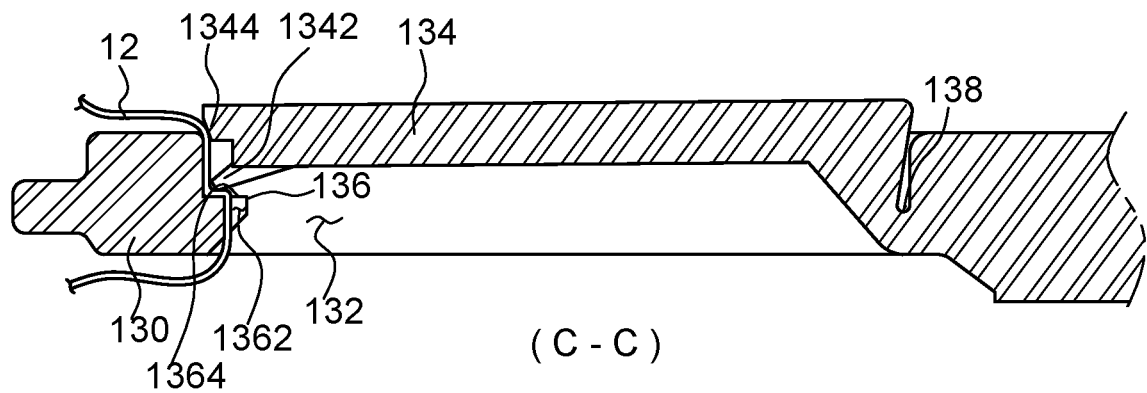
FIG. 12 is a cross-sectional view illustrating a cross section taken along line C-C of the buckle of FIG. 9.

FIG. 9 is a perspective view illustrating a state in which a strap is coupled to a buckle according to a second embodiment of the present disclosure, FIG. 10 is a perspective view illustrating a strap gripping protrusion formed at a fixing flap included in the buckle of FIG. 9, FIG. 11 is a diagram enlarging a strap connector of FIG. 9, and FIG. 12 is a cross-sectional view illustrating a cross section taken along line C-C of the buckle of FIG. 9.

In a buckle 100a of the present embodiment, a configuration of a strap connector 130 is different from that of the first embodiment described above, and the same configurations and reference numbers refer to the same as those of the first embodiment.

With reference to FIGS. 9 to 12, a strap connecting hole 132 with a rectangular shape may be formed at the strap connector 130 of the buckle 100a, and a fixing flap 134 with a cross-section of a rectangular shape, which is connected to one side wall forming the strap connecting hole 132 through a hinge 138, may be included in the strap connector 130. Also, a stepped portion 136 with which an end part 1344 of the fixing flap 134 selectively comes into contact may be formed to protrude inward from the strap connecting hole 132 at the other side wall thereof.

When the end part 1344 comes into contact with a stepped surface 1364 of the stepped portion 136, the fixing flap 134 may be pivoted centering on the hinge 138 to protrude outward from the strap connecting hole 132. Consequently, a wearer may pivot the fixing flap 134 to form a gap between the fixing flap 134 and the stepped portion 136 to pass an end part of the strap 12 through the strap connecting hole 132. Under such a state, the wearer may push the end part of the strap 12 in the gap to pass the strap 12 through the strap connecting hole 132, thereby connecting the buckle 100a to the strap 12.

The strap 12 passed as described above may be gripped by the end part 1344 of the fixing flap 134 and the stepped portion 136 so that a position of the strap 12 with respect to the buckle 100a may be fixed. And, more particularly, the strap 12 may be squeezed and gripped by pressure caused by which one or more strap gripping protrusions 1342, which are formed to protrude at the end part 1344 of the fixing flap 134, are inserted into one or more strap gripping depressions 1362 formed at the stepped portion 136.

For this purpose, at the stepped portion 136, the strap gripping depression 1362 may be formed to be concave at a position corresponding to the strap gripping protrusion 1342 from an inward surface of the strap connecting hole 132. Also, the strap gripping protrusion 1342 may be formed with a thickness corresponding to a width of the strap gripping depression 1362.

At this point, a restoring force (a torque) generated at the hinge 138 is delivered to the end part 1344 of the fixing flap 134 so that the pressure gripping the strap 12 may act thereon.

Also, the strap gripping protrusion 1342 may be formed to be inclined at a predetermined downward angle with respect to a surface of the fixing flap 134 facing the stepped surface 1364 of the stepped portion 136. With such a shape, the pressure gripping the strap 12 may be delivered thereto when the strap 12 is gripped, and thus the strap 12 may be firmly squeezed by the strap gripping protrusion 1342 and the strap gripping depression 1362 so that a gripped position of the strap 12 may be maintained.

In addition, when wanting to adjust a length of the strap 12, the wearer may pull a part of some of the strap 12 passing in a reverse direction against a direction to which the strap gripping protrusion 1342 protrudes, thereby sliding the strap 12 on an inclined surface of the strap gripping protrusion 1342 so that the length of the strap 12 may be easily adjusted in spite of the gripping pressure acting on the strap 12.

At this point, when wanting to adjust the length of the strap 12 in a reverse direction, the wearer may adjust the length by pulling the strap 12 in the reverse direction when a gap between the end part 1344 of the fixing flap 134 and the stepped portion 136 is formed by pivoting the fixing flap 134 by hand.

Meanwhile, the helmet 30 described above has a shape in which an outward surface of the tap 300 extends up to a bottom surface of the helmet 30 without being stopped by a brim 32 of the helmet 30. With such a shape, the buckles 100 and 100a according to the first and second embodiments can be inserted into the tap 300 from a bottom side of the helmet 30.

Figure 17:
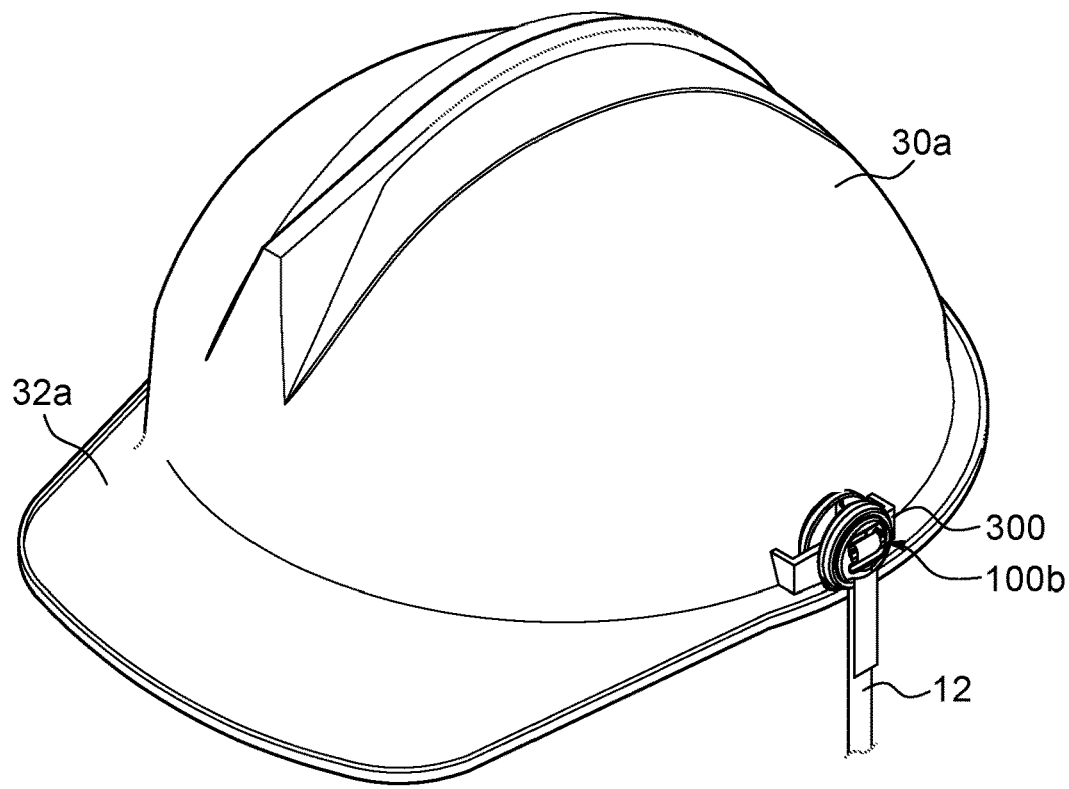
FIG. 17 is a perspective view illustrating a state in which the buckle of FIG. 13 is coupled to a helmet.

As shown in FIG. 17, however, when a helmet 30a has a shape in which a brim 32a extends farther in an outward direction than the outward surface of the tap 300, it may be very difficult to insert the buckles 100 and 100a according to the first and second embodiments from the bottom side of the helmet 30a due to interference from the brim 32a.

As described above, because the buckles 100 and 100a according to the first and second embodiments are difficult to use in the helmet 30a having a shape in which a width of a lateral portion of the brim 32a is wide and extends outward farther than the tap 300, a buckle 100b according to a third embodiment of the present disclosure is proposed to address such a problem described above and it will be described below.

Figure 13:
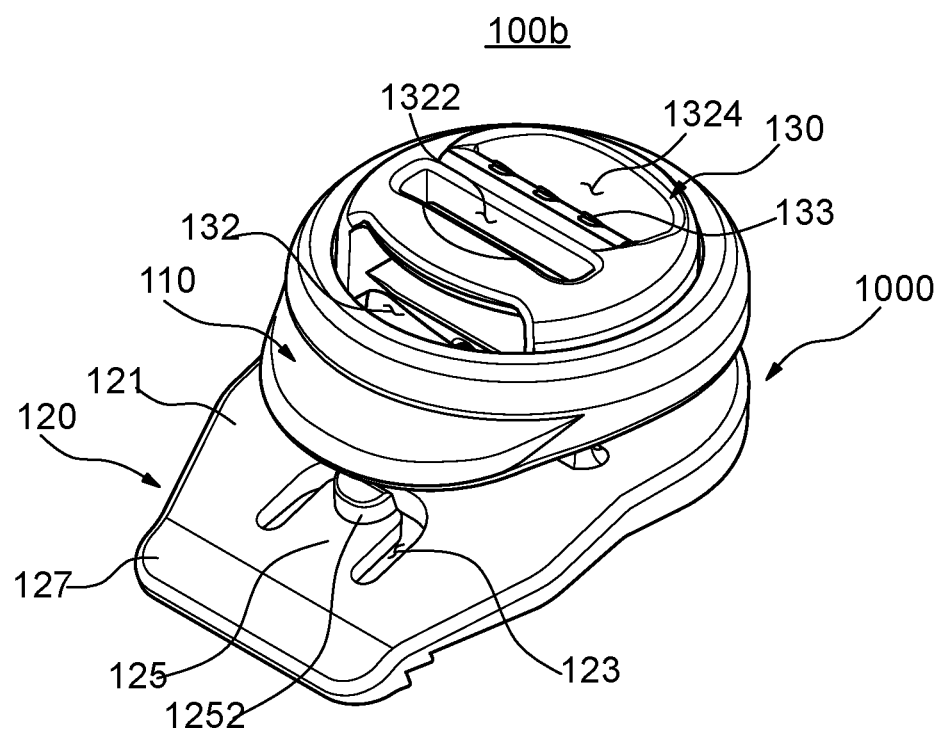
FIG. 13 is a perspective view illustrating a buckle according to a third embodiment of the present disclosure.
Figure 14:
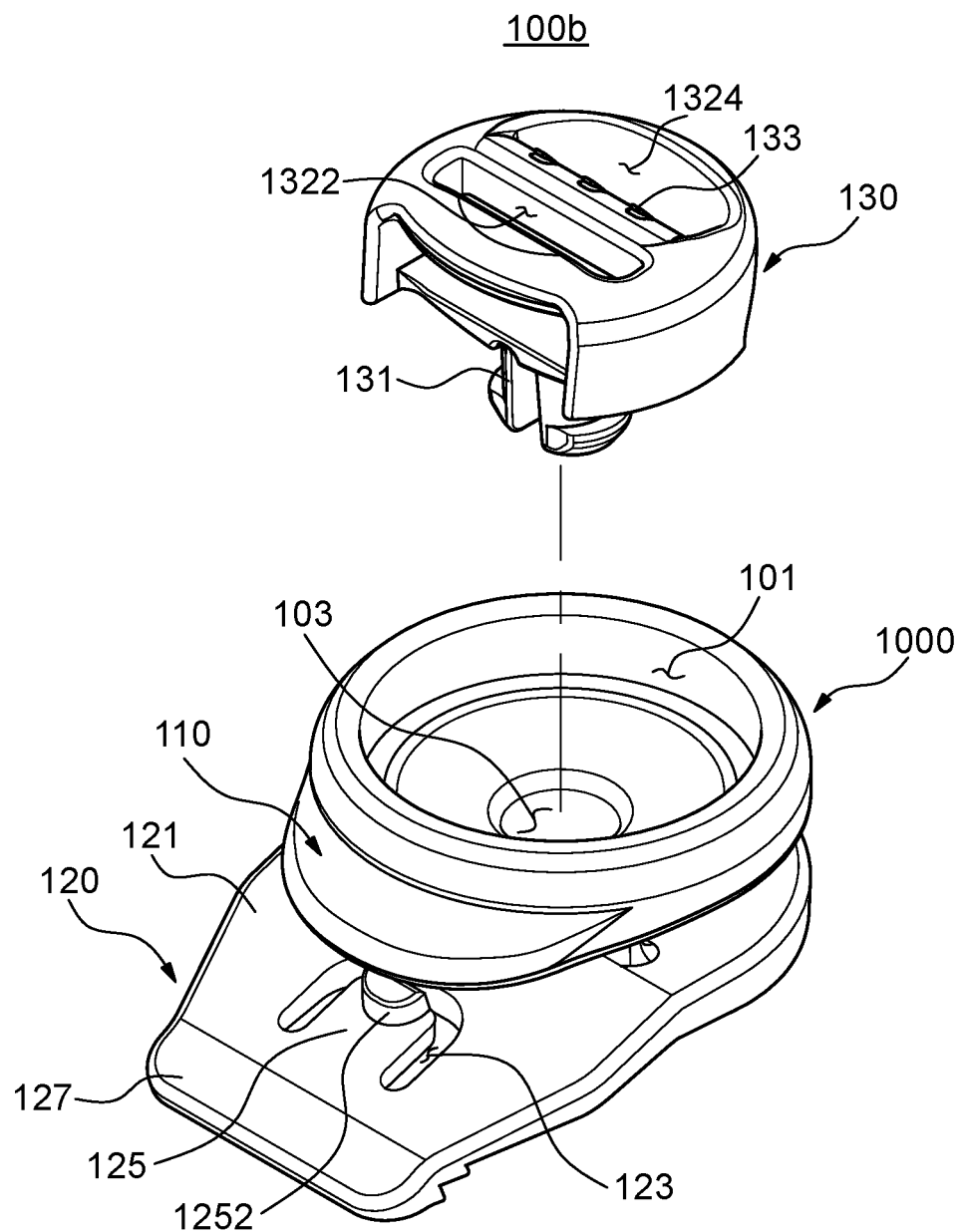
FIG. 14 is an exploded perspective view illustrating the buckle of FIG. 13 by exploding it.
Figure 15:
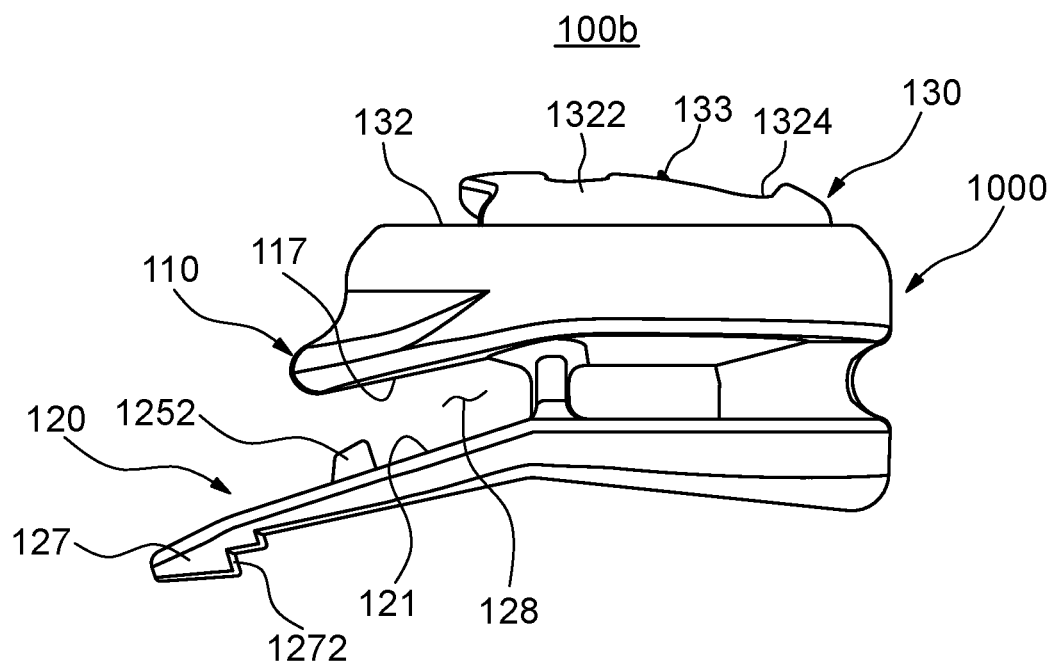
FIG. 15 is a lateral side view illustrating the buckle of FIG. 13.
Figure 16:
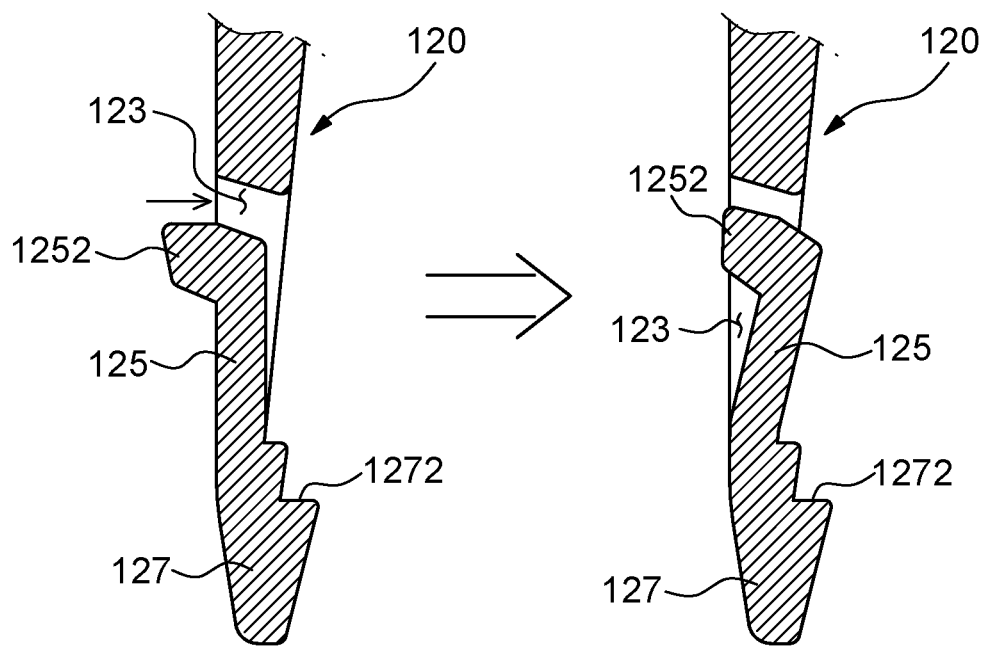
FIG. 16 is a diagram illustrating an action of a pressurizing protrusion of the buckle of FIG. 13.

Hereinafter, with reference to FIGS. 13 to 16, a detailed configuration of a buckle according to a third embodiment of the present disclosure will be described. FIG. 13 is a perspective view illustrating the buckle according to the third embodiment of the present disclosure, FIG. 14 is an exploded perspective view illustrating the buckle of FIG. 13 by exploding it, FIG. 15 is a lateral side view illustrating the buckle of FIG. 13, and FIG. 16 is a diagram illustrating an action of an elastic protrusion of the buckle of FIG. 13.

With reference to FIGS. 13 to 16, the buckle 100b according to the third embodiment is configured to enable a coupler 120 to enter from a top side of a tap 300 of a helmet 30a to an inner space of the tap 300, thereby being coupled thereto.

In particular, the buckle 100b may include a cylindrical-shaped main body 1000, a hooking portion 110 and a coupler 120 which are formed to protrude from the main body 1000, and a strap connector 130 to which a strap 12 is connected. Also, the tap 300 may be inserted into a separated space 128 formed between the hooking portion 110 and the coupler 120 so that the buckle 100b may be coupled to the helmet 30a. In addition, a circular-shaped accommodation space 101 at which an upper surface of the main body 1000 is opened may be formed at the main body 1000, and the strap connector 130 may have a shape that can be accommodated in the accommodation space 101 so that the strap connector 130 may be accommodated therein.

The coupler 120 may be formed to protrude to be inclined at a predetermined angle with respect to the main body 1000, and may form a V-shaped surface bent in an outward direction together with a surface opposite to an open surface of the accommodation space 101 of the main body 1000. Also, the hooking portion 110 may be formed to protrude approximately in parallel with the coupler 120 such that the separated space 128 may also be formed to be inclined at the predetermined angle with respect to the main body 1000.

In addition, a through hole 123 may be formed at a central portion of the coupler 120, and the coupler 120 may include a flexible member 125 accommodated inside the through hole 123. The through hole 123 may be formed in an approximately quadrangular shape, and the flexible member 125 may have a shape protruding from one of four inward surfaces of the through hole 123.

Moreover, a pressurizing protrusion 1252 protruding toward the hooking portion 110 may be formed at an end part of the flexible member 125. Consequently, as shown in FIG. 16, when a force pushing the pressurizing protrusion 1252 is applied from an external side, the flexible member 125 may be pivoted centering on a portion connected to the coupler 120 so that the pressurizing protrusion 1252 may be accommodated inside the through hole 123.

At an end part 127 of the coupler 120, a stepped surface 1272 may be formed at a surface opposite to a surface facing the hooking portion 110. Such a stepped surface 1272 is hooked at the tap 300 when the buckle 100b is inserted into the tap 300 of the helmet 30a, thereby serving to maintain a coupled state between the helmet 30a and the buckle 100b. In the present embodiment, the stepped surface 1272 of the end part 127 of the coupler 120 formed as two stages has been shown as an example, but this is merely one example and the stepped surface 1272 may be formed as a single stage or three or more stages.

The strap connector 130 may be generally configured in a cylindrical shape to include a coupling protrusion 131 protruding from a surface facing the accommodation space 101. A flange may be formed at an end part of the coupling protrusion 131, and the flange may prevent the strap connector 130 from escaping when the strap connector 130 is accommodated in the accommodation space 101. Also, a coupling hole 103 in which the coupling protrusion 131 may be accommodated is formed through a lower surface of the accommodation space 101. Consequently, the strap connector 130 may be provided not to be separated from a body of the buckle 100b and also to be rotatable when it is accommodated in the accommodation space 101.

The strap connector 130 may have a shape in which some portion of a circle forming an edge of an upper surface thereof is eliminated, and consequently, a strap connecting hole 132, which communicates with the accommodation space 101 when the strap connector 130 is accommodated in the accommodation space 101, may be formed. Through the strap connecting hole 132 formed as described above, an end part of the strap 12 may be inserted into the strap connector 130.

Also, a first strap coupling hole 1322 and a second strap coupling hole 1324 may be formed on the upper surface of the strap connector 130, the first strap coupling hole 1322 may be formed at a central portion of the strap connector 130, and the second strap coupling hole 1324 may be formed at a portion opposite to the strap connecting hole 132. In addition, all of the strap connecting hole 132, the first strap coupling hole 1322, and the second strap coupling hole 1324 may be formed to communicate with each other inside the strap connector 130.

The strap 12 may be inserted to pass through all of the strap connecting hole 132, the first strap coupling hole 1322, and the second strap coupling hole 1324, which are formed as described above, thereby being connected to the strap connector 130.

Also, one or more rubbing protrusions 133 may be formed to protrude between the first strap coupling hole 1322 and the second strap coupling hole 1324, and the strap 12 may not be easily released due to a friction force caused when a surface of the strap 12 comes into contact with the rubbing protrusions 133.

An action and an effect of the buckle 100b having the configuration described above according to the present embodiment will be described with reference to FIGS. 17 and 18. FIG. 17 is a perspective view illustrating a state in which the buckle of FIG. 13 is coupled to a helmet, and FIG. 18 is a cross-sectional view illustrating a state in which a strap is connected to the buckle of FIG. 13.

Figure 18:
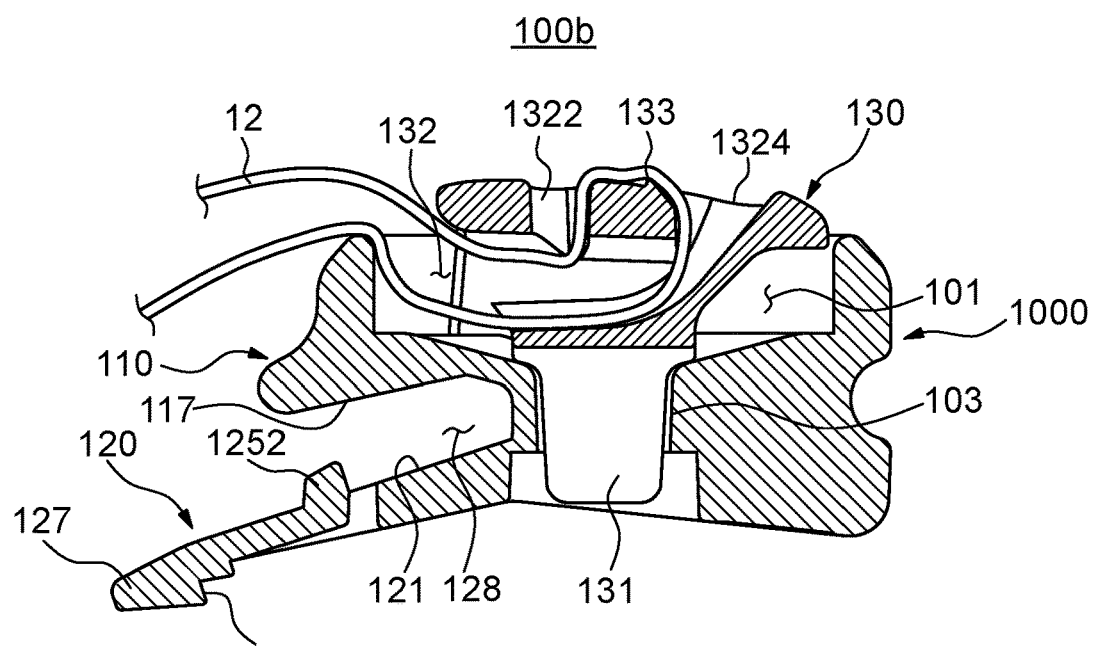
FIG. 18 is a cross-sectional view illustrating a state in which a strap is connected to the buckle of FIG. 13.

With reference to FIGS. 17 and 18, the buckle 100b according to the present embodiment may be fit into the tap 300 from a top side of the helmet 30a, and, at this point, the coupler 120 may be inserted into an inner space of the tap 300, thereby being coupled thereto.

Such a buckle 100b may be applicable to the helmet 30a having a shape in which the brim 32a protrudes toward the outside with respect to the tap 300 as shown in FIG. 17, and also to the helmet 30 having a shape in which the brim 32 does not protrude toward the outside with respect to the tap 300 as shown in FIG. 6.

In particular, when the coupler 120 of the buckle 100b enters into the tap 300 from the top side thereof, the pressurizing protrusion 1252 is pressed by the inward wall of the tap 300 and thus the flexible member 125 is pivoted so that the pressurizing protrusion 1252 may be accommodated inside the through hole 123 of the coupler 120.

Under such a state, when the entering of the coupler 120 into the tap 300 is completed, the stepped surface 1272 formed at the end part 127 of the coupler 120 is hooked at the tap 300 to prevent the coupler 120 from being separated in a reverse direction against an entering direction so that the coupled state of the buckle 100b with respect to the tap 300 may be maintained. At this point, the pressurizing protrusion 1252 may consistently apply a pressure, which is directed in a reverse direction against a pivoting direction, to the inward surface of the tap 300, and thus the coupled state of the buckle 100b with respect to the tap 300 may be firmly maintained.

Meanwhile, the strap 12 connected to the mask body 20 may be connected to the strap connector 130 of the buckle 100b, and more particularly, a free end of the strap 12 may be inserted through the strap connecting hole 132, and then the inserted free end thereof may again pass through the first strap coupling hole 1322, thereby protruding to the outside of the strap connector 130.

The strap connector 130 protruding as described above may be reinserted into the accommodation space 101 through the second strap coupling hole 1324, and the free end of the strap 12 passing through the second strap coupling hole 1324 may again pass through the strap connecting hole 132 to escape to the outside of the strap connector 130.

As described above, when the free end of the strap, which sequentially passed through and escaped from the strap connecting hole 132, the first strap coupling hole 1322, and the second strap coupling hole 1324, is tightly pulled, one surface of the strap 12 may be hooked by the rubbing protrusions 133 so that the strap 12 may be firmly connected to the strap connector 130.

In a state in which the strap 12 is connected to the strap connector 130, when the buckle 100b is inserted into the tap 300 through the process described above, the mask body 20 and the helmet 30a may be connected to each other through the strap 12 and the buckle 100b, and thus the mask body 20 may be maintained in a state of coming into close contact with a face of the wearer.

Also, because the strap connector 130 is rotatable against the main body 1000 of the buckle 100b, the strap connector 130 is rotated when the buckle 100b has been coupled to the tap 300 so that the strap connecting hole 132 may be located in a direction toward a position at which the strap 12 is connected to the mask body 20. Consequently, even though the buckle 100b is coupled to the helmet 30a and thus a position thereof is fixed, discomfort for the wearer due to a twist of the strap 12 may not be caused.

Meanwhile, when the wearer wants to separate the buckle 100b from the helmet 30a, he or she pushes the buckle 100b in an upward direction of the tap 300 while pressing the end part 127 of the coupler 120 in an inward direction of the tap 300 by hand, thereby separating the buckle 100b from the helmet 30a.

The following is a listing of the embodiments of the present disclosure.

Item 1 is a buckle for connecting a strap including a coupler configured to extend from one position, a strap connector at which a strap connecting hole is formed, wherein the strap connecting hole is connected to a strap which is connected to a mask body, and a hooking portion connected to the one position and including a surface configured to face the coupler, wherein a tap of a helmet or a tap of a head cradle is accommodated between the coupler and the hooking portion so that a position thereof is fixed.

Item 2 is the buckle for connecting a strap, which is provided to be connected to the tap of the head cradle to connect the head cradle to the strap, or to be connected to the tap of the helmet to connect the helmet to the strap.

Item 3 is the buckle for connecting a strap, in which the hooking portion includes a hook protrusion formed to protrude from the surface configured to face the coupler toward the coupler so as to narrow an opening of a space between the coupler and the hooking portion.

Item 4 is the buckle for connecting a strap, in which the hook protrusion is formed in a shape in which a cross sectional area thereof is gradually reduced in a direction protruding from the hooking portion, and an inward wall of the hook protrusion is stepped with respect to the surface configured to face the coupler of the hooking portion and an outward wall thereof is inclined with respect to the inward wall.

Item 5 is the buckle for connecting a strap, in which the hooking portion includes a protruding curved portion configured to protrude from the one position, an opposing curved portion configured to extend from the protruding curved portion so as to face the coupler, and an extending curved portion configured to extend from the opposing curved portion, wherein the hook protrusion is formed to protrude at a connection position between the opposing curved portion and the extending curved portion.

Item 6 is the buckle for connecting a strap, in which an end part of the extending curved portion is curved so as to approach a coupler.

Item 7 is the buckle for connecting a strap, in which a coupling depression is formed at the coupler to be concave from an outward end part thereof.

Item 8 is the buckle for connecting a strap, in which the coupler includes a central coupling member, and a side coupling member formed at both sides of the central coupling member, wherein the coupling depression is formed to define a boundary between the central coupling member and the side coupling member formed at the both sides thereof.

Item 9 is the buckle for connecting a strap, in which, when the tap of the helmet or the tap of the head cradle is accommodated between the coupler and the hooking portion, an end part of the tap of the helmet or the tap of the head cradle is maintained in a state of being hooked at a hook protrusion formed at the hooking portion.

Item 10 is the buckle for connecting a strap, in which the coupler includes a surface configured to face the hooking portion and formed to be inclined so as to gradually reduce a cross sectional area of the surface in a first direction.

Item 11 is the buckle for connecting a strap, in which the strap connecting hole is formed in a semicircular shape.

Item 12 is the buckle for connecting a strap, in which the strap connector includes a fixing flap connected to one side wall of the strap connecting hole, wherein a stepped portion with which an end part of the fixing flap selectively comes into contact is formed to protrude at the other side wall of the strap connecting hole.

Item 13 is the buckle for connecting a strap, in which the strap connector includes one or more strap gripping depressions formed to be concave at the stepped portion, and wherein the fixing flap includes a strap gripping protrusion formed to protrude at a position corresponding to the one or more strap gripping depressions from a surface configured to face the stepped portion.

Item 14 is the buckle for connecting a strap, in which the strap gripping protrusion is formed to be inclined with respect to a surface configured to face a stepped portion of the fixing flip.

Item 15 is the buckle for connecting a strap, in which each of the coupler, the hooking portion, and the strap connector has a symmetrical shape with respect to an imaginary central line extending in the first direction.

Item 16 is the buckle for connecting a strap which further includes a main body of a cylindrical shape, wherein the coupler and the hooking portion are formed to protrude from the main body, and the strap connector is provided as a member separated from the main body.

Item 17 is the buckle for connecting a strap, in which the coupler is formed in a shape which protrudes to be inclined at a predetermined angle with respect to the main body.

Item 18 is the buckle for connecting a strap, in which the coupler includes a flexible member accommodated inside a through hole formed at a center of the coupler and formed to protrude from one surface of a plurality of inward surfaces of the through hole, and a pressurizing protrusion configured to protrude toward the hooking portion at an end part of the flexible member.

Item 19 is the buckle for connecting a strap, in which a stepped surface is formed on a surface opposite to a surface facing the hooking portion at an end part of the coupler, and, when the coupler is inserted into and coupled to the tap of the helmet or the tap of the head cradle, the stepped surface is hooked at the tap of the helmet or the tap of the head cradle so that a coupled state with respect to the helmet is maintained.

Item 20 is the buckle for connecting a strap, in which an accommodation space of a circular shape in which an upper surface is opened is formed at the main body, and the strap connector is rotatably accommodated inside the accommodation space.

Item 21 is the buckle for connecting a strap, in which the strap connector includes a coupling protrusion configured to protrude from a surface facing the accommodation space, wherein a coupling hole to which the coupling protrusion is coupleable is formed at a lower surface of the accommodation space, and, when the strap connector is accommodated in the accommodation space, a state in which the coupling protrusion is inserted into the coupling hole is maintained.

Although the buckle for connecting a strap and the respirator harness including the same of the present disclosure have been described with reference to a number of concrete embodiments thereof, these embodiments are merely examples and the present disclosure is not limited thereto, and it should be construed that the embodiments have the full range of the basic spirit disclosed herein. Also, without departing from the scope of the present disclosure, those skilled in the art can implement a pattern of a shape not mentioned herein by combining and substituting the embodiments disclosed herein. In addition to the described above, those skilled in the art can easily change or modify the embodiments disclosed herein based on the description, and such changes or modifications should fall within the scope of the present disclosure defined by the appended claims.

The invention claimed is:
1. A mask assembly, comprising:
a strap;
a mask body connected to the strap; and
a buckle comprising:
a coupler configured to extend from one position wherein a coupling depression is formed at the coupler to be concave from an outward end part thereof and wherein the coupler includes a surface configured to face a hooking portion and formed to be inclined so as to gradually reduce a cross sectional area of the surface in a first direction;
a strap connector at which a strap connecting hole is formed, wherein the strap connecting hole is connected to the strap; and
the hooking portion connected to the one position and including a surface configured to face the coupler, wherein a tap of a helmet or a tap of a head cradle is accommodated between the coupler and the hooking portion so that a position thereof is fixed.

2. The mask assembly of claim 1, wherein the buckle is provided to be connected to the tap of the head cradle to connect the head cradle to the strap when the tap of the head cradle is accommodated between the coupler and the hooking portion, or to be connected to the tap of the helmet to connect the helmet to the strap when the tap of the helmet is accommodated between the coupler and the hooking portion.

3. The mask assembly of claim 2, wherein the hooking portion includes a hook protrusion formed to protrude from the surface configured to face the coupler toward the coupler so as to narrow an opening of a space between the coupler and the hooking portion.

4. The mask assembly of claim 3, wherein the hook protrusion is formed in a shape in which a cross sectional area thereof is gradually reduced in a direction protruding from the hooking portion, and an inward wall of the hook protrusion is stepped with respect to the surface configured to face the coupler of the hooking portion and an outward wall thereof is inclined with respect to the inward wall.

5. The mask assembly of claim 3, wherein the hooking portion includes:
a protruding curved portion configured to protrude from the one position;
an opposing curved portion configured to extend from the protruding curved portion so as to face the coupler; and
an extending curved portion configured to extend from the opposing curved portion,
wherein the hook protrusion is formed to protrude at a connection position between the opposing curved portion and the extending curved portion.

6. The mask assembly of claim 1, wherein the coupler includes:
a central coupling member; and
a side coupling member formed at both sides of the central coupling member,
wherein the coupling depression is formed to define a boundary between the central coupling member and the side coupling member formed at the both sides thereof.

7. The mask assembly of claim 6, wherein, when the tap of the helmet or the tap of the head cradle is accommodated between the coupler and the hooking portion, an end part of the tap of the helmet or the tap of the head cradle is maintained in a state of being hooked at a hook protrusion formed at the hooking portion.

8. The mask assembly of claim 1, wherein the strap connecting hole is formed in a semicircular shape.

9. The mask assembly of claim 1, wherein each of the coupler, the hooking portion, and the strap connector has a symmetrical shape with respect to an imaginary central line extending in the first direction.

10. A mask assembly, comprising:
a strap;
a mask body connected to the strap; and
a buckle comprising:
a coupler configured to extend from one position;
a strap connector at which a strap connecting hole is formed, wherein the strap connecting hole is connected to the strap and wherein the strap connector includes:
a fixing flap connected to one side wall of the strap connecting hole,
wherein a stepped portion with which an end part of the fixing flap selectively comes into contact is formed to protrude at the other side wall of the strap connecting hole; and
a hooking portion connected to the one position and including a surface configured to face the coupler,
wherein a tap of a helmet or a tap of a head cradle is accommodated between the coupler and the hooking portion so that a position thereof is fixed.

11. The mask assembly of claim 10, wherein the strap connector includes:
one or more strap gripping depressions formed to be concave at the stepped portion, and
wherein the fixing flap includes:
a strap gripping protrusion formed to protrude at a position corresponding to the one or more strap gripping depressions from a surface configured to face the stepped portion.

12. The mask assembly of claim 11, wherein the strap gripping protrusion is formed to be inclined with respect to a surface configured to face the stepped portion of the fixing flap.

13. A mask assembly, comprising:
a strap;
a mask body connected to the strap; and
a buckle comprising:
a main body of a cylindrical shape;
a coupler configured to extend from one position;
a strap connector at which a strap connecting hole is formed, wherein the strap connecting hole is connected to the strap; and
a hooking portion connected to the one position and including a surface configured to face the coupler,
wherein the coupler and the hooking portion are formed to protrude from the main body, and the strap connector is provided as a member separated from the main body,
wherein a tap of a helmet or a tap of a head cradle is accommodated between the coupler and the hooking portion so that a position thereof is fixed.

14. The mask assembly of claim 13, wherein the coupler is formed in a shape which protrudes to be inclined at a predetermined angle with respect to the main body.

15. The mask assembly of claim 13, wherein the coupler includes:
a flexible member accommodated inside a through hole formed at a center of the coupler and formed to protrude from one surface of a plurality of inward surfaces of the through hole; and
a pressurizing protrusion configured to protrude toward the hooking portion at an end part of the flexible member.

16. The mask assembly of claim 13, wherein a stepped surface is formed on a surface opposite to a surface facing the hooking portion at an end part of the coupler, and, when the coupler is inserted into and coupled to the tap of the helmet or the tap of the head cradle, the stepped surface is hooked at the tap of the helmet or the tap of the head cradle so that a coupled state with respect to the helmet is maintained.

17. The mask assembly of claim 13, wherein an accommodation space of a circular shape in which an upper surface is opened is formed at the main body, and the strap connector is rotatably accommodated inside the accommodation space.

18. The mask assembly of claim 17, wherein the strap connector includes:
a coupling protrusion configured to protrude from a surface facing the accommodation space, wherein a coupling hole to which the coupling protrusion is couplable is formed at a lower surface of the accommodation space, and, when the strap connector is accommodated in the accommodation space, a state in which the coupling protrusion is inserted into the coupling hole is maintained.

* * * * *